(12) United States Patent
Zhang et al.

(10) Patent No.: US 8,362,422 B2
(45) Date of Patent: Jan. 29, 2013

(54) SAMPLE FEEDING DEVICE FOR ION MOBILITY SPECTROMETER, METHOD OF USING THE SAME AND ION MOBILITY SPECTROMETER

(75) Inventors: Qingjun Zhang, Beijing (CN); Zhiqiang Chen, Beijing (CN); Shiping Cao, Beijing (CN); Yuanjing Li, Beijing (CN); Ziran Zhao, Beijing (CN); Yinong Liu, Beijing (CN); Yan Zheng, Beijing (CN); Shaoji Mao, Beijing (CN); Xiang Zou, Beijing (CN); Jianping Chang, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 65 days.

(21) Appl. No.: 13/142,500

(22) PCT Filed: Apr. 27, 2011

(86) PCT No.: PCT/CN2011/073390
§ 371 (c)(1),
(2), (4) Date: Jun. 28, 2011

(87) PCT Pub. No.: WO2012/088809
PCT Pub. Date: Jul. 5, 2012

(65) Prior Publication Data
US 2012/0168616 A1 Jul. 5, 2012

(30) Foreign Application Priority Data
Dec. 31, 2010 (CN) .......................... 2010 1 0624243

(51) Int. Cl.
*H01J 49/40* (2006.01)
*H01J 49/14* (2006.01)
*G01N 27/64* (2006.01)

(52) U.S. Cl. ........ 250/288; 250/281; 250/282; 250/287; 250/286

(58) Field of Classification Search .................. 250/288, 250/281, 282, 287, 286
See application file for complete search history.

(56) References Cited

U.S. PATENT DOCUMENTS 5,053,343 A * 10/1991 Vora et al. ...................... 436/153
7,968,842 B2 * 6/2011 Zapata et al. .................. 250/288
(Continued)

FOREIGN PATENT DOCUMENTS

| CN | 2927049 Y | 7/2007 |
| CN | 201130166 Y | 10/2008 |
| EP | 1 471 343 A1 | 10/2004 |

OTHER PUBLICATIONS

Search Report and Written Opinion from PCT Application No. PCT/CN2011/073390, dated Oct. 13, 2011, 9 pgs.

*Primary Examiner* — Nikita Wells
(74) *Attorney, Agent, or Firm* — Westman, Champlin & Kelly, P.A.

(57) ABSTRACT

The present invention discloses a sample feeding device for an ion mobility spectrometer, which is adapted to guide a sample to be detected into an inlet of a drift tube of the ion mobility spectrometer. The sample feeding device comprises a solid sample feeding component; a sample inlet component; a attachment component, wherein the solid sample feeding component has an internal cavity defined therein, one end of the solid sample feeding component is communicated with the sample inlet component through the internal cavity, while the other end is communicated with the inlet of the ion drift tube through the attachment component; and a gaseous sample feeding component, comprising a body and an external attachment component, the body has a gas channel therein, and the external attachment component includes an inlet hole which is communicated with the gas channel, wherein when the external attachment component is fitted with the sample inlet component, the body is inserted into the internal cavity, so that a channel of the solid sample feeding component is closed, and only the gas channel of the gaseous sample feeding component is communicated with the inlet of the drift tube of the ion mobility spectrometer.

10 Claims, 4 Drawing Sheets

U.S. PATENT DOCUMENTS 8,013,297 B2 * 9/2011 Peng et al. .................... 250/296
8,237,110 B2 * 8/2012 Peng et al. .................... 250/286
2004/0155181 A1 8/2004 Krasnobaev et al. ......... 250/288

* cited by examiner

SAMPLE FEEDING DEVICE FOR ION MOBILITY SPECTROMETER, METHOD OF USING THE SAME AND ION MOBILITY SPECTROMETER

CROSS-REFERENCE TO RELATED APPLICATION

This Application is a Section 371 National Stage Application of International Application No. PCT/CN2011/073390, filed Apr. 27, 2011 and not yet published, which claims the benefit of Chinese Patent Application No. 201010624243.4 filed on Dec. 31, 2010 in the State Intellectual Property Office of China, the whole contents of which are hereby incorporated by reference in their entirety.

BACKGROUND OF THE INVENTION

1. Field of the Invention

The present invention relates to an ion mobility detecting technique. More particularly, the present invention relates to a sample feeding device for an ion mobility spectrometer and a method for detecting solid and gaseous samples using the sample feeding device. In addition, the present invention also relates to an ion mobility spectrometer having the sample feeding device.

2. Description of the Related Art

Currently commercially available detectors for safety inspection mainly detect harmful substances such as explosives and narcotics by an ion mobility spectrometry. Such detectors comprise a sample feeding device.

The sample feeding device can gasify and desorb solid particles or gas entering into the device. The gasified sample molecules are then introduced into an ionization region by air flow. After that, the ionized sample molecules enter into a drift region. The molecules are identified based on their drift time in the drift region. The actual sample feeding devices are classified as both a gaseous sample feeding device and a solid sample feeding device. A sample collecting paper or a sample collecting rod is provided for the solid sample feeding device. Trace residual substance is collected by wiping a surface of an object under inspection with the collecting paper, and then the collecting paper or the sample collecting rod is inserted into the solid sample feeding device, and thereby information about the residual substance on the surface of the object is obtained through detection. In contrast, the gaseous sample feeding device directly extracts gas released by an object under inspection to detect substance. An early commercially available detector typically has function of feeding only one type of sample, for example SMITH's desktop Ionscan 5000DT only having solid sample feeding function. Recently, in order to improve the ability of the sample feeding device, Sample feeding devices with both gaseous and solid sample feeding ability are commercially available. Furthermore, a portion of patents has been applied to the product, for example SABER EXV, SABER 4000, and MMTD of SMTH, whose characteristic is to employ two separate sample feeding inlets. When detecting gaseous sample, it is needed to insert a PTFE sheet at a solid sample feeding inlet to close a sample feeding gas path. The disadvantage of SABER 4000 is that the volume of the sample feeding device is large, and occupies one fifth space of the detector. However, the sample feeding device in the desktop detector generally only has the solid sample feeding ability. These factors make constraint to the miniaturization of the detector and restrict the function of the product.

In viewing of the above, there is a need in the prior art to develop a practical ion mobility spectrometer with solid and gaseous sample feeding apparatus. On one hand, the ion mobility spectrometer has a built-in concentrating device so as to simplify its arrangement and operation procedure; and on the other hand, the detector can sensitively and conveniently detect trace level of the residual solid on the object under inspection and gas with an extremely low concentration.

SUMMARY OF THE INVENTION

Therefore, an object of the present invention is to solve at least one of the above problems and defects in the prior art.

In accordance with an aspect of the present invention, there is provided a sample feeding device for an ion mobility spectrometer, which is adapted to guide a sample to be detected into an inlet of a drift tube of the ion mobility spectrometer. This sample feeding device can feed both gaseous sample and solid sample. Since the sample feeding device only has one sample feeding inlet, the design of the sample feeding device is simplified, and the volume of the corresponding device becomes relatively small. Therefore, this sample feeding device is capable of applying in both portable detectors and desktop detectors.

The sample feeding device comprises: a solid sample feeding component, a sample inlet component, an attachment component, and a gaseous sample feeding component. The solid sample feeding component has an internal cavity defined therein, one end of the solid sample feeding component is communicated with the sample inlet component through the internal cavity, while the other end of the solid sample feeding component is communicated with the inlet of the ion drift tube through the attachment component; the gaseous sample feeding component comprises a body and an external attachment component, the body has a gas channel therein, and the external attachment component includes an inlet hole which is communicated with the gas channel, wherein when the external attachment component is fitted with the sample inlet component, the body is inserted into the internal cavity, so that a channel of the solid sample feeding component is closed, while only the gas channel of the gaseous sample feeding component is communicated with the inlet of the drift tube of the ion mobility spectrometer.

Preferably, the sample inlet component comprises a guide groove and a photo diode. When a solid sample sheet enters into the internal cavity through the guide groove, the photo diode detects the sample and then sends a trigger signal.

Preferably, the sample feeding device further comprises a semi-permeable membrane component, which comprises a suction hole, a mounting, a locking hoop and a semi-permeable membrane, wherein a position of the suction hole of the semi-permeable membrane component corresponds to that of a suction hole of a suction component, and the locking hoop has an annular outer periphery. The semi-permeable membrane is secured to the mounting by the annular outer periphery and an outer surface of the locking hoop is sealed against the suction component.

In one preferred embodiment of the present invention, the internal cavity is in a flat shape, a central portion of the internal cavity is in the form of arc and two ends of the internal cavity on both side of the central portion are in the form of square. The body of the gaseous sample feeding component has a cylindrical shape.

Preferably, the flat-like shape has a height between 1 and 10 mm, and a width between 15 and 50 mm.

Furthermore, the sample feeding device further comprises a suction component, which is attached to the attachment component, thereby forming a suction gas flow in order to remove the gaseous sample not entering into the inlet of the drift tube by suction.

In accordance with another aspect of the present invention, there is provided a method of guiding a solid sample to be detected by using the sample feeding device of the ion mobility spectrometer, comprising: detaching the gaseous sample feeding component; inserting the solid sample into the internal cavity of the solid sample feeding component through the guide groove of the sample inlet component; sending out a trigger signal by the photo diode after the photo diode detects the solid sample to start a heating component disposed outside the internal cavity and the ion mobility spectrometer; vaporizing the solid sample in the internal cavity, and guiding the vaporized solid sample into the inlet of the drift tube of the ion mobility spectrometer through the internal cavity; and detecting the sample within the ion mobility spectrometer.

In accordance with yet another aspect of the present invention, there is provided a method of guiding a gaseous sample to be detected by using the sample feeding device of the ion mobility spectrometer, comprising: inserting the gaseous sample feeding component; sucking the gaseous sample to be detected into the body of the gaseous sample feeding component through an gas inlet; guiding the gaseous sample to be detected into the inlet of the drift tube of the ion mobility spectrometer through the gas channel of the gaseous sample feeding component; and detecting the sample within the ion mobility spectrometer.

In addition, the present invention further provides an ion mobility spectrometer, comprising: a drift tube adapted to ionize and drift the sample to be detected which is guided into the ion mobility spectrometer; and the sample feeding device adapted to guide the sample to be detected into the inlet of the drift tube.

The above non-specific embodiments of the present invention have at least one or more of the following advantages and effects:

The sample feeding device of the present invention has both solid and gaseous sample feeding function. Since only one sample feeding inlet is employed, it is possible to reduce the volume and space of the sample feeding device and to effectively reduce the volume of the ion mobility spectrometer. The sample feeding modes are switched by inserting and removing the gaseous sample feeding component so that the sample feeding device can simply and conveniently switch between the gaseous and solid sample feeding modes.

DETAILED DESCRIPTION OF THE EMBODIMENTS

The technical solution of the present invention is further explained in detail through the embodiment taken in conjunction with the FIGS. 1-7 of the accompanying drawings. Throughout the specification, the same or similar reference number is designated as the component having the same or similar function. The description of the present embodiment is intended to explain the generally inventive concept of the present invention below with reference to the accompanying drawings, rather than is interpreted as a limitation to the present invention.

Figure 3:
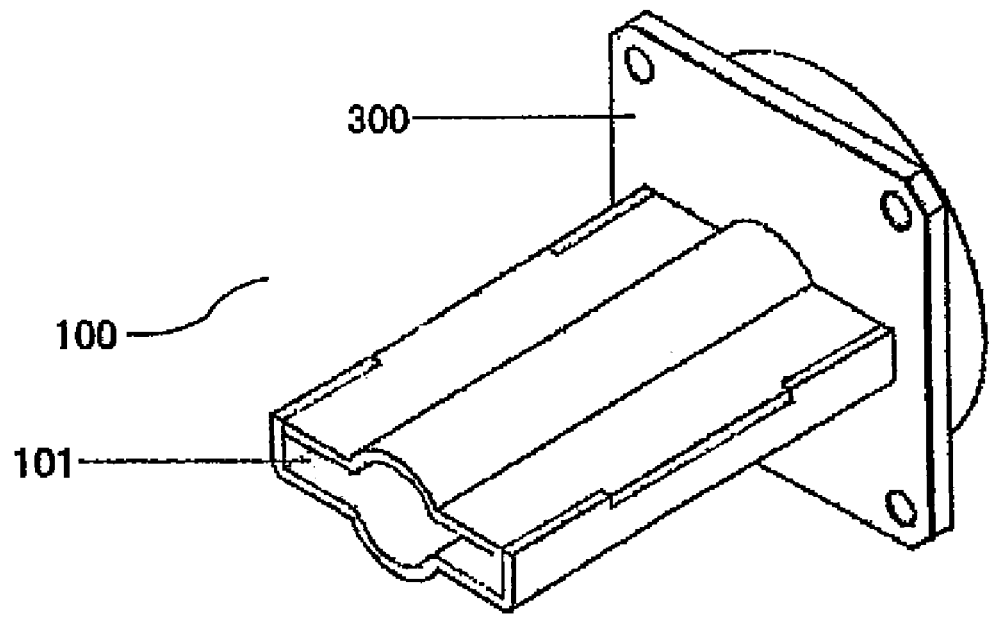
FIG. 3 is a schematic view showing a solid sample feeding component and an attachment component assembled together according to an embodiment of the present invention.
Figure 4:
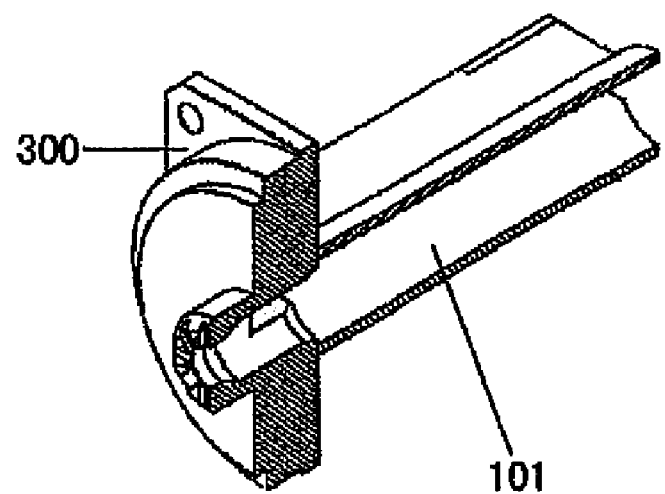
FIG. 4 is a cross sectional view showing the solid sample feeding component and the attachment component assembled together according to the embodiment of the present invention.
Figure 5:
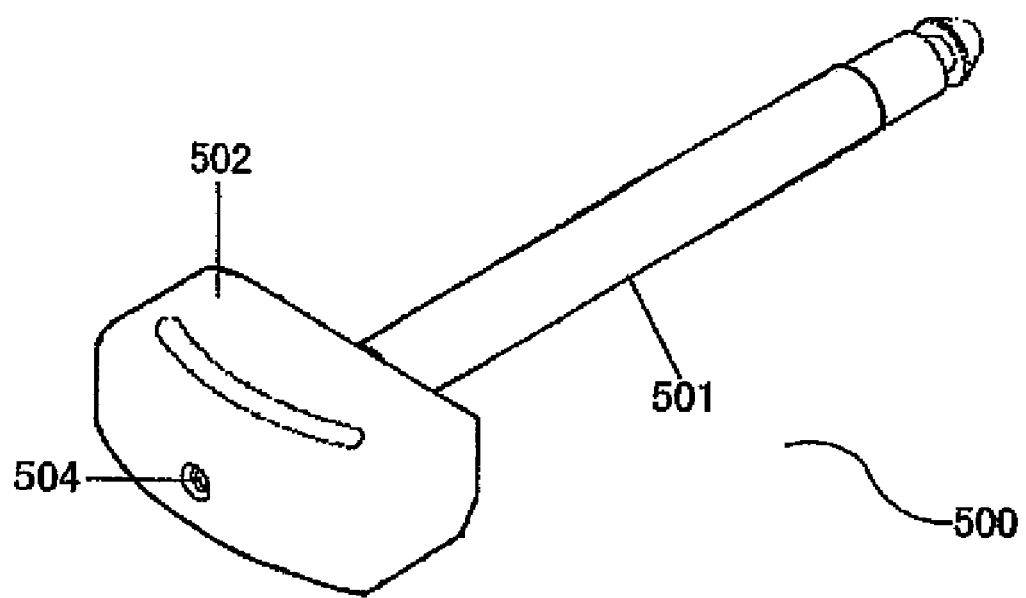
FIG. 5 is a schematic view showing a gaseous sample feeding component according to an embodiment of the present invention.

As shown in FIGS. 1-5, a sample feeding device 10 includes: a solid sample feeding component 100, a sample inlet component 200, a attachment component 300, and a gaseous sample feeding component 500. The solid sample feeding component 100 has an internal cavity 101 (shown in FIG. 3 in detail) defined therein. One end of the solid sample feeding component 100 is communicated with the sample inlet component 200 through the internal cavity 101, while the other end of the solid sample feeding component 100 is communicated with an inlet 400 of an ion drift tube through the attachment component 300. The gaseous sample feeding component 500 includes a body 501 and an external attachment component 502 (as shown in FIG. 5 in detail). The body 501 has a gas channel 503 therein, and the external attachment component 502 includes an inlet hole 504 which is communicated with the gas channel 503. When the external attachment component 502 is fitted with the sample inlet component 200, the body 501 is inserted into the internal cavity 101, so that a channel of the solid sample feeding component 100 is closed, while only the gas channel 503 of the gaseous sample feeding component 500 is communicated with the inlet 400 of the drift tube of the ion mobility spectrometer.

Figure 2:
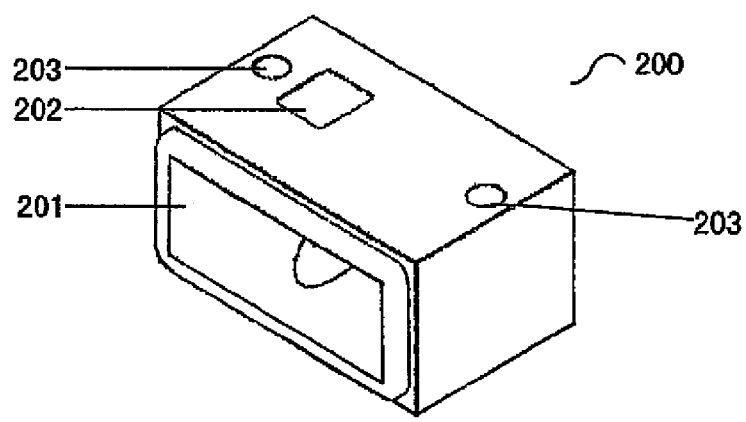
FIG. 2 is a schematic view showing a sample inlet component according to an embodiment of the present invention.

In accordance with the preferred embodiment of the present invention, as shown in FIG. 2, it shows the sample inlet component 200. The sample inlet component 200 includes a guide groove 201 and a photo diode 202. When a solid sample sheet enters into the internal cavity 101 through the guide groove 201, the photo diode 202 detects the sample and then sends a trigger signal. Furthermore, an installation hole 203 may be disposed in the sample inlet component. The sample inlet component 200 is assembled with other components by the installation hole 203. A person skilled in the art also can assemble the sample inlet component with other components by using other conventional means. In addition, the guide groove 201 has a relatively large opening, so that the collecting paper is easily inserted into the solid sample inlet component 200. A radiator is disposed at the photo diode 202, so that the photo diode 202 always operates at a relative low temperature for ensuring the detector performance.

As shown in FIGS. 3-5, in accordance with one preferred embodiment of the present invention, the internal cavity 101 is in a flat-like shape. Specifically, a central portion of the internal cavity 101 is in the form of arc and two ends of the internal cavity on both sides of the central portion are in the form of square. Correspondingly, the body 501 of the gaseous sample feeding component 500 is cylindrical. In this way, it can ensure that solid sample feeding efficiency is not affected and the gaseous sample feeding function can also be performed. The flat-like shape has a height between 1 and 10 mm, and a width between 15 and 50 mm. In the present embodiment, the flat-like shape has a height of 3 mm and a width of 22 mm.

Figure 1:
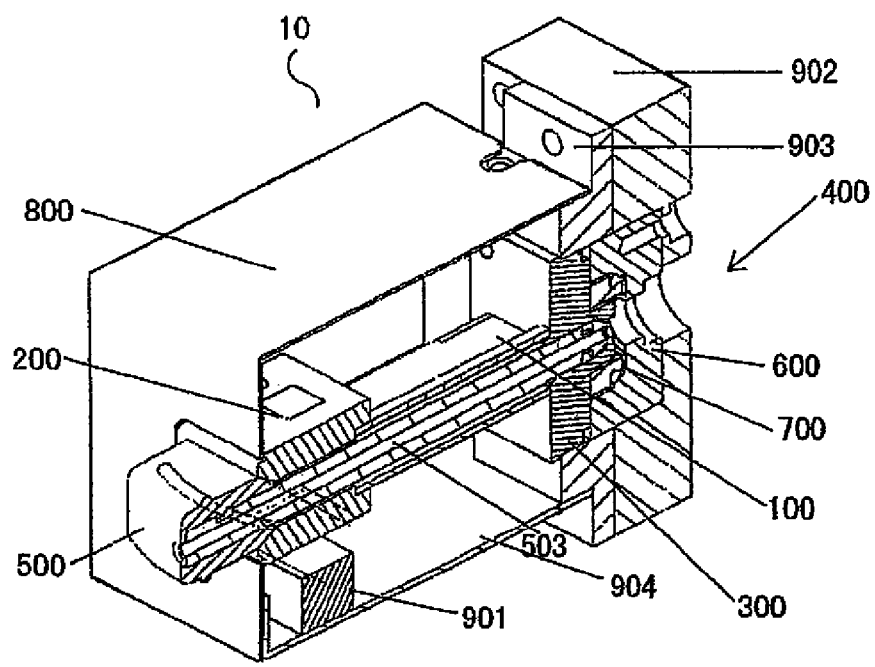
FIG. 1 is a cross sectional view of a sample feeding device according to an embodiment of the present invention.
Figure 6:
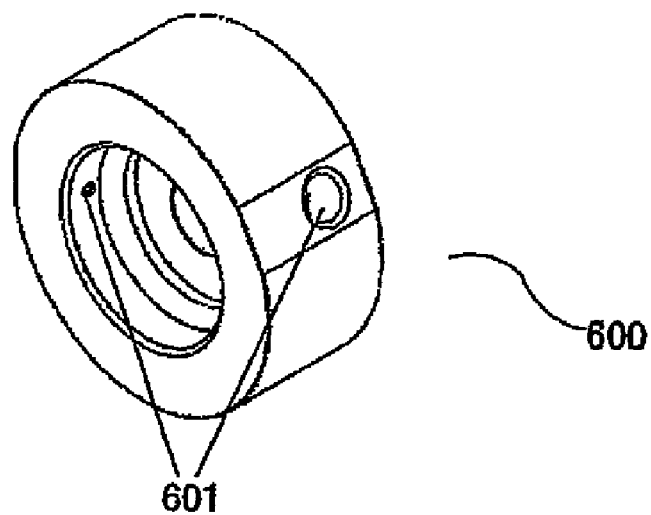
FIG. 6 is a schematic view showing a suction component according to an embodiment of the present invention.
Figure 7:
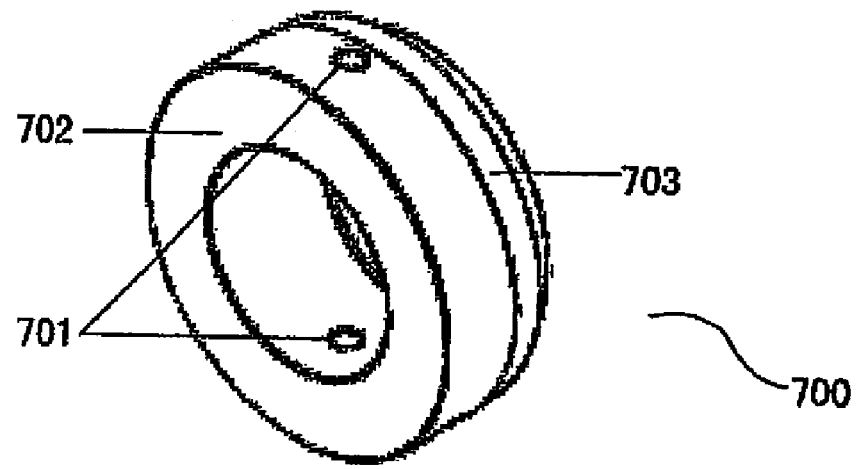
FIG. 7 is a schematic view showing a semi-permeable membrane component according to an embodiment of the present invention.

FIGS. 6 and 7 are schematic views showing a suction component 600 and a semi-permeable membrane 700, respectively. In one preferred embodiment, the suction component 600 includes suction holes 601. As shown in FIG. 1, the suction component 600 is attached to the attachment component 300, thereby forming a suction gas flow in order to remove the gaseous sample not entering into the inlet of the drift tube by suction. It should be understood that the arrangement and construction of the suction component are described herein only as an example, and thus the person skilled in the art can employ any other conventional technical means in the art to remove the gaseous sample not entering into the inlet of the drift tube by suction.

The sample feeding device of the present invention also includes a semi-permeable membrane disposed between the inlet 400 of the drift tube and the end of the channel of the internal cavity. The semi-permeable membrane can be disposed on the semi-permeable membrane component 700 as shown in FIG. 7. The semi-permeable membrane component 700 includes suction holes 701 of which a position correspond to a position of the suction holes 601 of the suction component. The semi-permeable membrane component 700 further includes auxiliary components such as a mounting 702, and a locking hoop 703 to support and secure the semi-permeable membrane. The mounting 702 is made of metal material, and employs aluminium plated with nickel in the present embodiment. The locking hoop 703 is made of fluorine rubber (or medical-grade silicone rubber), which is resistant to high temperature and does not emit gaseous foreign substance. Since the material of locking hoop 703 can be resistant to high temperature, i.e. the fluorine rubber is resistant to high temperature of 250° C., it does not adhere to the metal surface. The annular outer periphery is capable of securing the soft semi-permeable membrane onto the mounting 702, while ensuring the tightness. It is ensured that the interior of the drift tube is sealed by sealing an outer planar surface of the locking hoop 703 against the suction component 600. A high-temperature state of the semi-permeable membrane is obtained by heat conducted from the sample inlet and the drift tube. It should be understood that the arrangement and construction of the semi-permeable membrane are described herein only as an example, and thus the person skilled in the art can employ any other conventional technical means in the art to achieve this function.

As shown in FIG. 6, a recess of the suction component 600 is used to house the semi-permeable membrane component 700. A gas flow in front of the semi-permeable membrane is pumped out by two suction holes 601.

Furthermore, the sample feeding device of the present invention also includes auxiliary components such as an upper cover 800, stay plates 901 and 902, an attachment member 903, and a bottom plate 904 for supporting and attaching. The sample feeding device 10 is attached to the drift tube by the attachment member 903. Moreover, sealing devices are disposed between the semi-permeable membrane component and the fixation sample feeding component, the gaseous sample feeding component as well as the inlet of the drift tube to achieve the air-tightness. Since the person skilled in the art can design and produce those components by the conventional technical means in the art, in combination with the practical situation, and those components are not a main part of the present invention, these are not described in detail.

When detecting a solid sample, it should be vaporized. Thus, the solid sample feeding component 100 has the function of quickly heating sample. Generally, heating components are disposed outside the internal cavity, for example by winding the heating filaments, so that the internal cavity 101 is always kept at a high temperature. Alternatively, the sample is vaporized by using laser in the internal cavity 101 for an instant. In one preferred embodiment of the present invention, the electrically heating filaments are employed and the internal cavity 101 is surrounded by thermal insulation material, so that the temperature of the solid sample feeding component 100 is kept at 180° C. all the time.

In addition, a surface of metal component in the gas path passing the gas is polished or plated with nickel, so that the surface is smooth, thereby reducing the absorption of the gas by the metal component.

Operations of detecting the solid sample and gaseous sample by using the sample feeding device of the present invention are described below:

In a solid sample feeding mode (the gaseous sample feeding component 500 is detached), after a collecting paper with the sample passes through the sample inlet component 200 with the guide groove 201, the photo diode 202 detects the solid sample, and the photo diode sends a trigger signal to start the ion mobility spectrometer. The solid sample is vaporized in the internal cavity 101, and the vaporized sample flows into the inlet 400 of the ion mobility spectrometer through the internal cavity, and the sample is detected within the ion mobility spectrometer.

In a gaseous sample feeding mode (the gaseous sample feeding component 500 is inserted), the detecting steps are as follows: the gaseous sample to be detected is input into the body 501 of the gaseous sample feeding component 500 through the gas inlet 504; the gaseous sample to be detected is guided into the inlet 400 of the drift tube of the ion mobility spectrometer through the gas channel of the gaseous sample feeding component 500; and the gaseous sample is detected in the ion mobility spectrometer. Because the channel of the solid sample feeding component is closed, the gaseous sample is guided in the front of the semi-permeable membrane only through the gas channel of the gaseous sample feeding component, and then enters into the inlet of the drift tube; and the gaseous sample feeding component 500 is kept at a high temperature since the gaseous sample feeding component 500 is located in the high-temperature internal cavity 101.

In accordance with one preferred embodiment of the present invention, the process of detecting the sample to be detected by the ion mobility spectrometer including the above sample feeding device includes the following steps:

When performing the solid sample feeding function, the collecting paper is inserted into the guide groove 201, so that after entering the solid sample feeding component 100, the sample is quickly heated up and becomes sample vapour. This sample vapour reaches the semi-permeable membrane component under the action of the gas flow, and a gas flow mass which runs at a high speed and has a large surface area, is formed in front of the semi-permeable membrane. A part of the sample enters into the interior of the drift tube by penetrating through the semi-permeable membrane, and is entrained by the gas flow in the interior of the drift tube to enter into an ionization region. The ions of the ionized sample (which are actually charged sample cluster, and referred to as sample ions hereinafter) reach a collecting electrode under the action of the drift electric field. Further, the sample is identified based on the ion drift time.

When performing gaseous sample feeding function, the gaseous sample feeding component 500 is inserted into the solid sample feeding component 100, and the channel of the solid sample feeding component 100 is closed, while only the gas channel of the gaseous sample feeding component 500 acts. Under the action of a high speed suction gas flow, the gaseous sample reaches the semi-permeable membrane after passing through the channel of the gaseous sample feeding component 500. Similarly, a gas flow mass which runs at a high speed and has a large surface area, is formed in the front of the semi-permeable membrane. The sample penetrating through the semi-permeable membrane enters into the ionization region and the drift region so as to be analyzed, thereby obtaining the information about the substance component.

Although some embodiments of the general inventive concept are illustrated and explained, it would be appreciated by those skilled in the art that modifications and variations may be made in these embodiments without departing from the principles and spirit of the overall inventive concept of the disclosure, the scope of which is defined in the claims and their equivalents.

What the claims is:

1. A sample feeding device for an ion mobility spectrometer, which is adapted to guide a sample to be detected into an inlet of a drift tube of the ion mobility spectrometer, the sample feeding device comprising:
   a solid sample feeding component;
   a sample inlet component;
   a attachment component, wherein the solid sample feeding component has an internal cavity defined therein, one end of the solid sample feeding component is communicated with the sample inlet component through the internal cavity, while the other end of the solid sample feeding component is communicated with the inlet of the ion drift tube through the attachment component; and
   a gaseous sample feeding component, comprising a body and an external attachment component, wherein the body has a gas channel therein, and the external attachment component includes an inlet hole which is communicated with the gas channel, wherein when the external attachment component is fitted with the sample inlet component, the body is inserted into the internal cavity, so that a channel of the solid sample feeding component is closed, and only the gas channel of the gaseous sample feeding component is communicated with the inlet of the drift tube of the ion mobility spectrometer.

2. The sample feeding device for the ion mobility spectrometer according to claim 1, characterized in that:
   the sample inlet component comprises a guide groove and an photo diode, when a solid sample sheet enters the internal cavity through the guide groove, the photo diode detects the sample and then sends a trigger signal.

3. The sample feeding device for the ion mobility spectrometer according to claim 1, characterized in that:
   the sample feeding device further comprises a semi-permeable membrane component, which comprises a suction hole, a mounting, a locking hoop and a semi-permeable membrane,
   wherein a position of the suction hole corresponds to a position of a suction hole of a suction component, the locking hoop has an annular outer periphery, the semi-permeable membrane is secured to the mounting by the annular outer periphery and an outer surface of the locking hoop is sealed against the suction component.

4. A method of guiding a solid sample to be detected by using the sample feeding device for an ion mobility spectrometer as claimed in claim 3, comprising:
   detaching the gaseous sample feeding component;
   inserting a solid sample into the internal cavity of the solid sample feeding component through the guide groove of the sample inlet component;
   sending out a trigger signal by a photo diode after the photo diode detects the solid sample to start a heating component disposed outside the internal cavity and the ion mobility spectrometer;
   vaporizing the solid sample in the internal cavity, and guiding the vaporized solid sample into the inlet of the drift tube of the ion mobility spectrometer through the internal cavity; and
   detecting the sample within the ion mobility spectrometer.

5. The sample feeding device for the ion mobility spectrometer according to claim 1, characterized in that:
   the internal cavity has a flat shape, a central portion of the internal cavity is in the form of arc and two ends of the internal cavity on both sides of the central portion are in the form of square.

6. The sample feeding device for the ion mobility spectrometer according to claim 5, characterized in that:
   the flat-like shape has a height between 1 and 10 mm, and a width between 15 and 50 mm.

7. The sample feeding device for the ion mobility spectrometer according to claim 6, characterized in that:
   the body of the gaseous sample feeding component is in a cylindrical shape.

8. The sample feeding device for the ion mobility spectrometer according to claim 1, characterized in that:
   the sample feeding device further comprises a suction component, which is attached to the attachment component, thereby forming a suction gas flow so as to remove the gaseous sample not entering the inlet of the drift tube by suction.

9. A method of guiding a gaseous sample to be detected by using the sample feeding device for the ion mobility spectrometer as claimed in claim 1, comprising:
   inserting the gaseous sample feeding component;
   inputting a gaseous sample to be detected into the body of the gaseous sample feeding component through a gas inlet;
   guiding the gaseous sample to be detected into the inlet of the drift tube of the ion mobility spectrometer through the gas channel of the gaseous sample feeding component; and
   detecting the sample within the ion mobility spectrometer.

10. An ion mobility spectrometer, comprising:
    a drift tube adapted to ionize and drift a sample to be detected which is guided into the ion mobility spectrometer; and
    a sample feeding device as claimed in claim 1, adapted to guide the sample to be detected into an inlet of the drift tube.

* * * * *